United States Patent
Radosevich

(10) Patent No.: US 7,329,743 B2
(45) Date of Patent: Feb. 12, 2008

(54) GENE ENCODING LABYRINTHIN, A MARKER FOR CANCER

(75) Inventor: James Radosevich, Rockford, IL (US)

(73) Assignee: ImmvaRx, Inc., Rockford, IL (US)

( * ) Notice: Subject to any disclaimer, the term of this patent is extended or adjusted under 35 U.S.C. 154(b) by 223 days.

(21) Appl. No.: 10/830,702

(22) Filed: Apr. 23, 2004

(65) Prior Publication Data

US 2005/0208508 A1 Sep. 22, 2005

Related U.S. Application Data

(60) Division of application No. 09/659,521, filed on Sep. 12, 2000, now Pat. No. 6,727,080, which is a continuation of application No. PCT/US99/05365, filed on Mar. 11, 1999, which is a continuation-in-part of application No. 09/040,485, filed on Mar. 17, 1998, now Pat. No. 6,166,176.

(51) Int. Cl.
C12N 15/11 (2006.01)
(52) U.S. Cl. ...................... 536/23.2; 536/23.1
(58) Field of Classification Search ............... None
See application file for complete search history.

(56) References Cited

U.S. PATENT DOCUMENTS 5,728,819 A * 3/1998 Jacobs et al. .............. 536/23.5

OTHER PUBLICATIONS

NCBI Accession No. U03109 (Nov. 30, 1995).*
Dinchuk, J.E., et al. (2000) "Aspartyl beta-hydroxylase (Asph) and an evolutionalrily conserved isoform of Asph missing the catalytic domain share exons with junctin." *Journal of Biological Chemistry* 275(50):39543-39554.
Engelhardt, S., et al., (2001). "Early impairment of calcium handling and altered expression of junction in hearts of mice overexpressing the beta 1-adrenergic receptor." *FASEB Journal* 15(14):2718-2720.
Froemming, G.R. and Ohlendieck, K. (2001) "Native skeletal muscle dihydropyridine receptor exists as a supramolecular triad complex." *Cell. Mol. Life Sci.* 58:312-320.
Glover, L., et al. (2001) "Calsequestrin binds to monomeric and complexed forms of key calcium-handling proteins in native sarcoplasmic reticulum membranes from rabbit skeletal muscle." *Biochimica et Biophysica Acta.* 1515(2):120-132.
Jones, L.R., et al., (1995) "Purification, primary structure, and immunological charaterization of the 26-kDa calsequestrin binding protein (junctin) from cardiac junctional sarcoplasmic reticulum." *Journal of Biological Chemistry* 270(51):30787-30796.
Jones, L.R., et al. (1998) "Regulation of Ca2+ signaling in transgenic mouse cardiac myocytes overexpressing calsequestrin." *Journal of Clinical Investigation.* 101(7):1385-1393.
Kagari, T., et al. (1996) "Biochemical characterization of calsequestrin-binding 30-kDa protein in sarcoplasmic reticulum of skeletal muscle." *Biochemical & Biophysical Research Communications.* 227(3):700-706.

Kirchhefer, U., et al. (2001) "Cardiac hypertrophy and impaired relaxation in transgenic mice overexpressing triadin 1." *Journal of Biological Chemistry.* 276(6):4142-4149.
Kiriazis, H. and Kranias, E.G. (2000) "Genetically engineered models with alterations in cardiac membrane calcium-handling proteins." *Annual Review of Physiology.* 62:321-351.
Kobayashi, Y.M., et a.l. (2000) "Localization and Characterization of the Calsequestrin-binding Domain of Triadin 1." *Journal of Biological Chemistry.* 275(23):17639-17646.
Kobayashi, Y.M. and Jones, L.R. (1999) "Identification of triadin 1 as the predominant triadin isoform expressed in mammalian myocardium." *Journal or Biological Chemistry.* 274(40):28660-28668.
Kohler, S.A., et al. (1995) "Succinate dehydrogenase b mRNA of *Drosophila melanogaster* has a functional iron-responsive element in its 5'-untranslated region." *Journal of Biological Chemistry.* 270(51):30781-30786.
Lim, K.Y., et al. (2000) "cDNA cloning and characterization of human cardiac junctin." *Gene.* 255(1):35-42.
Luss, I., et al. (1999) "Expression of cardiac calcium regulatory proteins in atrium v ventricle in different species." *Journal of Molecular & Cellular Cardiology.* 31(6):1299-1314.
Nori, A., et al. (1999) "Targeting of calsequestrin to sarcoplasmic reticulum after deletions of its acidic carboxy terminus." *American Journal of Physiology.* 277(5 Pt 1):C974-981.
Ohlendieck, K. (2000) "Changes in $Ca^{2+}$-Regulatory Muscle Membrane Proteins During the Chronic Low-Frequency Stimulation Induced Fast-To-Slow Transition Process," *Basic Appl. Myol.* 10(3):99-106.
Sato, Y., et al.(1998) "Cardiac-specific overexpression of mouse cardiac calsequestrin is associated with depressed cardiovascular function and hypertrophy in transgenic mice." *Journal of Biological Chemistry.* 273(43):28470-28477.
Shin, D.W., et al. (2000) "The asp-rich region at the carboxyl-terminus of calsequestrin binds to CA(2+) and interacts with triadin." *FEBS Letters* 486(2):178-182.
Shorofsky, S.R., et al. (1999) "Cellular mechanisms of altered contractility in the hypertrophied heart: big hearts, big sparks." *Circulation Research.* 84(4):424-434.

(Continued)

*Primary Examiner*—Misook Yu
(74) *Attorney, Agent, or Firm*—Barnes & Thornburg LLP; Alice O. Martin

(57) ABSTRACT

A cDNA molecule that encodes a protein designated Labyrinthin (Lab) is isolated and its nucleotide sequence is determined. The protein, or peptides derived from the protein, are markers useful to define novel classes of cancers. Diagnostic assays for these cancers use antibodies to Lab or nucleotide probes that hybridize with the lab gene or a fragment therefrom. Vaccines useful either to prevent recurrence of cancers in subjects who test positive for Lab (or lab), or to prevent initial occurrence of cancer, use proteins or peptides derived from Lab. Expression of Lab via immunogenic assays is used to monitor effects of cancer treatments. Antisense molecules against lab are used in treatments. Sense molecules of lab are used to restore lost lab function in diseased normal cells, for example, gland cells.

4 Claims, 3 Drawing Sheets

OTHER PUBLICATIONS

Treves, S., et al. (2000) "Molecular cloning, expression, functional characterization, chromosomal localization, and gene structure of junctate, a novel integral calcium binding protein of sarco (endo)plasmic reticulum membrane." *Journal of Biological Chemistry.* 275(50):39555-39568.

Wetzel, G.T., et al.(2000) "Molecular cloning of junctin from human and developing rabbit heart." *Molecular Genetics & Metabolism.* 69(3):252-258.

Yamaguchi, N. and Michiki, K. (1998) "Identification of 30 kDa calsequestrin-binding protein, which regulates calcium release from sarcoplasmic reticulum of rabbit skeletal muscle." *Biochem. J.* 335:541-547.

Zhang, L. et al. (1997) "Complex Formation between Junctin, Triadin, Calsequestrin, and the Ryanodine Receptor." *Journal of Biological Chemistry.* 272(37):23389-23397.

* cited by examiner

Fig. 1

```
CGGGAGCTTGAAGGACACAAGAATGGGAGGAAAGGCGGACTCTCAGGAAC     (Ribosome Binding Site)
TTCATTCTTCACGTGGTTTATGGTGATTGCATTGCTGGGCGTCTGGACAT     (Start Codon)
CTGTAGCTGTCGTTTGGTTTGATCTTGTTGACTATGAGGAAGTTCTAGGA
AAACTAGGAATCTATGATGCTGATGGTGATGGAGATTTTGATGTGGATGA
TGCCAAAGTTTTATTAGGACTTAAAGAGAGATCTACTTCAGAGCCAGCAG
TCCCGCCAGAAGAGGCTGAGCCACACACTGAGCCCGAGGAGCAGGTTCCT
GTGGAGGCAGAACCCCAGAATATCGAAGATGAAGCAAAAGAACAAATTCA
GTCCCTTCTCCATGAAATGGTACACGCAGAACATGTTGAGGGAGAAGACT
TGCAACAAGAAGATGGACCCACAGGAGAACCACAACAAGAGGATGATGAG
TTTCTTATGGCGACTGATGTAGATGATAGATTTGAGACCCTGGAACTTGA
AGTATCTCATGAAGAAACCGAGCATAGTTACCACGTGGAAGAGACAGTTT
CACAAGACTGTAATCAGGATATGGAAGAGATGATGTCTGAGCAGGAAAAT
CCAGATTCCAGTGAACCAGTAGTAGAAGATGAAAGATTGCACCATGATAC
AGATGATGTAACATACCAAGTCTATGAGGAACAAGCAGTATATGAACCTC
TAGAAAATGAAGGGATAGAAATCACAGAAGTAACTGTCCCCCCTGAGGAT
AATCCTGTAGAAGATTCACAGGTAATTGTAGAAGAAGTAAGCATTTTTCC
TGTGGAAGAACAGCAGGAAGTACCACCAGATACTTAAAGCTTCAAAAAGA     (Stop Codon)
CTGCCCCTACCACCACAGGAGGACCAGCCTAACCATACGCTCCAAAAGAT
GGCTGTGATAGATCTTGTGAAGCAATTACTGAGCAGATCAAGATCTTTGG
GAAGGAACACTAAAGATGTTTTGAATGAATTATAGTCCACTGGCATTTTA
GTGTATTTTTTTTCTTTTTAGAAACACACATTTCTAAAAATGTCATGTT
ACATTCCTGCATGTCCCTTTTGATAGCATTAGTGGATCCATTGGATTTCT
TTTTTCTTTTTGTGAGACAGCTTTTAGTCTTACCTGAATTTATGTGTGTT     (Instability Sequence)
TTTCCGACAGTGGTTAATAATTATATTGGTGATGTAGCAGCAATTGTGTT
GGCAGGGTTTTCATATATTATTAGTAATTAACACTAACTGTTGGACTGAC
TTGTGTACACTGTGTTAAACATGATTTAAAAGCTATTAAGAGTACTTTGT     (Instability Sequence)
GTTAGCACTCTTAAAAACGCTAACAGAGATCATCATTAGCTGTGAAGATT
TGAGTTGTATATACCTGCACTGATATTCTTATCAAAAATTTCTACATTAG
CTTTAAGTGTTCAGATTAACACTTTTGAAACCTTTGTAGCTTTTAGCTGA
TTAATTAGAAAAATTAATATTTCAGTGAAAGTTTTAAATTATCATTTATT     (Instability Sequence)
TATTTTTTTAAATGAGAGGGGAAAGCTGAAATTCCTTGTTAAGACACAAG
GAAAAGAATGGCCCTACTATTATCATGCAAAAATGCTTTGTTGGCACCT
CAGATTAATCATATAATAGCTATAGTCTCTTCAGCATTTGTTTAAATTTT
AGAAAACCTGTATAAATTACTGGTGCATAACTTAAAGATTATTCTGCCTT
TGGCTAATTGAGTAATTCCCCTCCAGCACTAGAGACCGCTCAGTGCTCTT
ACTAGATGAACTCAGTAACGCCTTGAGCTGGGTTGATTGAGGATGTGTGA
AAAAGCTCACAGAGCCCGATGCCTGCTGCTATTTCACGGCAATGAGCCTT
TTTCTTTCTACACTGAAGATTTTCTTCTTATTTAATGTGGTTTATTTTGG     (Instability Sequence)
GCTCAGAAATAATTGCTCTGTTGAAAATAATCCTTTGTCAGAAAAGAAGG
TAGCTACCACATCATTTTGAAAGGACCATGAGCAACTATAAGCAAAGCCA
TAAGAAGTGGTTTGATCGATATATTAGGGGTAGCTCTTGATTTTGTTAAC
ATTAAGATAAGGTGACTTTTTCCCCCTGCTTTTAGGATTAAAATCAAAGA     (Sub-optimal Poly-
TACTTCTATATTTTTATCACTATAGATCATAGTTATTATACAATGTAGTG      adenylation Site)
AGTCCTGCATGGGTACTCGATGTGTAATGAAACCTGAAATAATAATAAGA
TAATAAGAAAAGCAATAATTTTCTAAAGCTGTGCTGTCGGTGATACAGAG
ATGATACTCAAATTATAATAAAACTCTTCATTTTGTGAATTATAGAAGCT     (Optimal Polyadeny-
ACTTTTTATAAAGCCATATTTTTTTAGGGAAACTAAGGAGTGACATAGAA      lation Site)
CTGATGAATGAGTAAAAGTAAGTTTTGCTGGATTTTTGTAGAACTCTGGA
CGTTGAGGATTCATTATGCTGTGGTTAACTTTAAATATTTT  (SEQ ID NO: 1)
```

Fig. 2

MVIALLGVWTSVAVVWFDLVDYEEVLGKLGIYDADGDGDFDVDDAKVLLGLK

ERSTSEPAVPPEEAEPHTEPEEQVPVEAEPQNIEDEAKEQIQSLLHEMVHAE

HVEGEDLQQEDGPTGEPQQEDDEFLMATDVDDRFETLEPEVSHEETEHSYHV

EETVSQDCNQDMEEMMSEQENPDSSEPVVEDERLHHDTDDvtyqvyeeqavY
                                            <--MAD I-->

EPLENEGIEITEVTAPPEDNPVEDSQviveevsifpvEEQQEVPPDT
    <--MAD II-->

Predicted Ca++ Binding Region (SEQ ID NO: 2) VLGKLGIYDADGDGDFDVDDAKVLLGLK (SEQ ID NO: 3) Parvalbumin        vkkafaiidqdksgfieedelklflqnf
(SEQ ID NO: 4) Calmodulin         fkeafslfdkagdgtittkelgtvmrsl
(SEQ ID NO: 5) Troponin-C         ladcfrtfdknadgfidieelgeilrat Ca++ Binding Residues            *  *  *    *    *
    Required Residue                        +

---

SYMBOL KEY:

BOLD = Eukaryotic Leader Sequence

_____ = Myristylation Site
  ^ lower case = Membrane Anchoring Domain (MAD)
<-------->

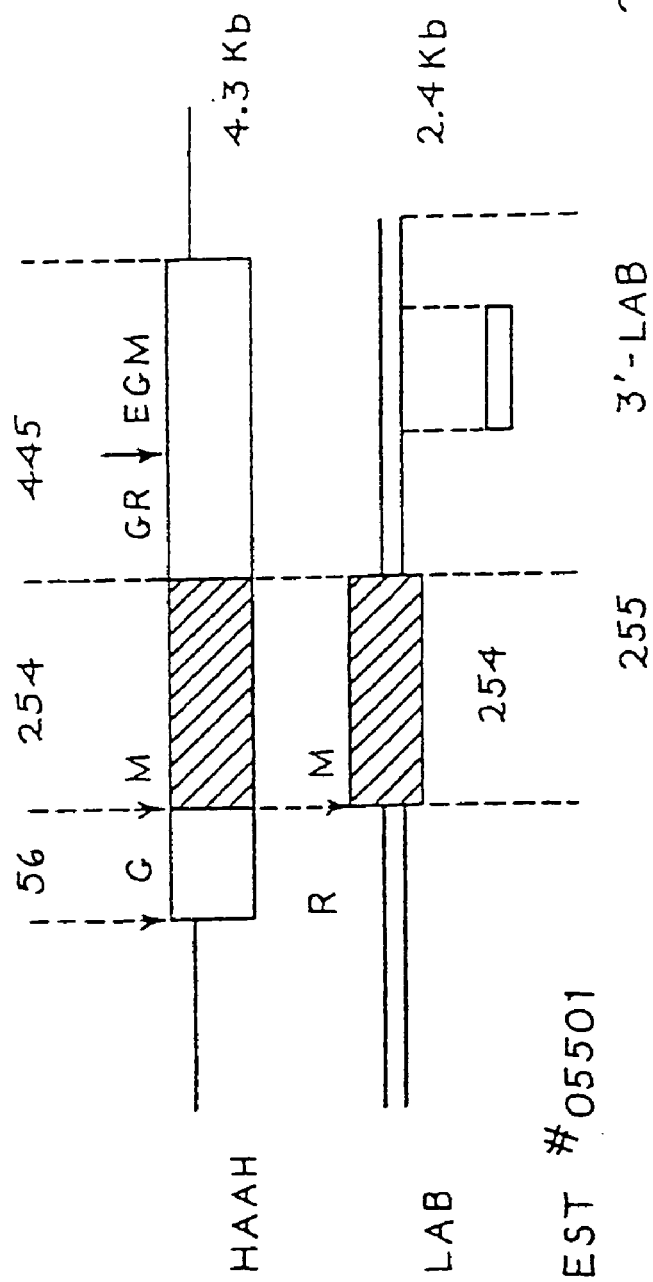

SEQUENCE LISTING

<160> NUMBER OF SEQ ID NOS: 10

<210> SEQ ID NO 1
<211> LENGTH: 2442
<212> TYPE: DNA
<213> ORGANISM: Homo sapiens
<220> FEATURE:
<221> NAME/KEY: CDS
<222> LOCATION: (70)..(834)

<400> SEQUENCE: 1

```
cgggagcttg aaggacacaa gaatgggagg aaaggcggac tctcaggaac ttcattcttc        60 acgtggttt  atg gtg att gca ttg ctg ggc gtc tgg aca tct gta gct gtc     111
           Met Val Ile Ala Leu Leu Gly Val Trp Thr Ser Val Ala Val
             1               5                  10 gtt tgg ttt gat ctt gtt gac tat gag gaa gtt cta gga aaa cta gga        159
Val Trp Phe Asp Leu Val Asp Tyr Glu Glu Val Leu Gly Lys Leu Gly
 15              20                  25                  30 atc tat gat gct gat ggt gat gga gat ttt gat gtg gat gat gcc aaa        207
Ile Tyr Asp Ala Asp Gly Asp Gly Asp Phe Asp Val Asp Asp Ala Lys
             35                  40                  45 gtt tta tta gga ctt aaa gag aga tct act tca gag cca gca gtc ccg        255
Val Leu Leu Gly Leu Lys Glu Arg Ser Thr Ser Glu Pro Ala Val Pro
 50                  55                  60 cca gaa gag gct gag cca cac act gag ccc gag gag cag gtt cct gtg        303
Pro Glu Glu Ala Glu Pro His Thr Glu Pro Glu Glu Gln Val Pro Val
         65                  70                  75 gag gca gaa ccc cag aat atc gaa gat gaa gca aaa gaa caa att cag        351
Glu Ala Glu Pro Gln Asn Ile Glu Asp Glu Ala Lys Glu Gln Ile Gln
     80                  85                  90 tcc ctt ctc cat gaa atg gta cac gca gaa cat gtt gag gga gaa gac        399
Ser Leu Leu His Glu Met Val His Ala Glu His Val Glu Gly Glu Asp
 95                 100                 105                 110 ttg caa caa gaa gat gga ccc aca gga gaa cca caa caa gag gat gat        447
Leu Gln Gln Glu Asp Gly Pro Thr Gly Glu Pro Gln Gln Glu Asp Asp
                115                 120                 125 gag ttt ctt atg gcg act gat gta gat gat aga ttt gag acc ctg gaa        495
Glu Phe Leu Met Ala Thr Asp Val Asp Asp Arg Phe Glu Thr Leu Glu
            130                 135                 140 ctt gaa gta tct cat gaa gaa acc gag cat agt tac cac gtg gaa gag        543
Leu Glu Val Ser His Glu Glu Thr Glu His Ser Tyr His Val Glu Glu
        145                 150                 155 aca gtt tca caa gac tgt aat cag gat atg gaa gag atg atg tct gag        591
Thr Val Ser Gln Asp Cys Asn Gln Asp Met Glu Glu Met Met Ser Glu
    160                 165                 170 cag gaa aat cca gat tcc agt gaa cca gta gta gaa gat gaa aga ttg        639
Gln Glu Asn Pro Asp Ser Ser Glu Pro Val Val Glu Asp Glu Arg Leu
175                 180                 185                 190 cac cat gat aca gat gat gta aca tac caa gtc tat gag gaa caa gca        687
His His Asp Thr Asp Asp Val Thr Tyr Gln Val Tyr Glu Glu Gln Ala
                195                 200                 205 gta tat gaa cct cta gaa aat gaa ggg ata gaa atc aca gaa gta act        735
Val Tyr Glu Pro Leu Glu Asn Glu Gly Ile Glu Ile Thr Glu Val Thr
            210                 215                 220 gtc ccc cct gag gat aat cct gta gaa gat tca cag gta att gta gaa        783
Val Pro Pro Glu Asp Asn Pro Val Glu Asp Ser Gln Val Ile Val Glu
        225                 230                 235 gaa gta agc att ttt cct gtg gaa gaa cag cag gaa gta cca cca gat        831
Glu Val Ser Ile Phe Pro Val Glu Glu Gln Gln Glu Val Pro Pro Asp
    240                 245                 250
```

```
                240                 245                 250
act taaagcttca aaaagactgc ccctaccacc acaggaggac cagcctaacc        884
Thr
255 atacgctcca aaagatggct gtgatagatc ttgtgaagca attactgagc agatcaagat  944 ctttgggaag gaacactaaa gatgttttga atgaattata gtccactggc attttagtgt 1004 attttttttt cttttagaa acacacattt ctaaaaatgt catgttacat tcctgcatgt  1064 cccttttgat agcattagtg gatccattgg atttcttttt tctttttgtg agacagcttt  1124 tagtcttacc tgaatttatg tgtgttttc cgacagtggt aataattat attggtgatg    1184 tagcagcaat tgtgttggca gggttttcat atattattag taattaacac taactgttgg  1244 actgacttgt gtacactgtg ttaaacatga tttaaaagct attaagagta ctttgtgtta  1304 gcactcttaa aaacgctaac agagatcatc attagctgtg aagatttgag ttgtatatac  1364 ctgcactgat attcttatca aaatttcta cattagcttt aagtgttcag attaacactt   1424 ttgaacctt tgtagctttt agctgattaa ttagaaaaat taatatttca gtgaaagttt    1484 taaattatca tttatttatt tttttaaatg agagggaaa gctgaaattc cttgttaaga    1544 cacaaggaaa aagaatggcc ctactattat catgcaaaaa tgctttgttg gcacctcaga   1604 ttaatcatat aatagctata gtctcttcag catttgttta aatttagaa aacctgtata    1664 aattactggt gcataactta aagattattc tgcctttggc taattgagta attccctcc    1724 agcactagag accgctcagt gctcttacta gatgaactca gtaacgcctt gagctgggtt   1784 gattgaggat gtgtgaaaaa gctcacagag cccgatgcct gctgctattt cacggcaatg   1844 agccttttc tttctacact gaagattttc ttcttattta atgtggttta ttttgggctc    1904 agaaataatt gctctgttga aaataatcct ttgtcagaaa agaaggtagc taccacatca   1964 ttttgaaagg accatgagca actataagca aagccataag aagtggtttg atcgatatat   2024 tagggggtagc tcttgatttt gttaacatta agataaggtg actttttccc cctgctttta  2084 ggattaaaat caaagatact tctatattt tatcactata gatcatagtt attatacaat    2144 gtagtgagtc ctgcatgggt actcgatgtg taatgaaacc tgaataata ataagataat    2204 aagaaaagca ataattttct aaagctgtgc tgtcggtgat acagagatga tactcaaatt   2264 ataataaaac tcttcatttt gtgaattata gaagctactt tttataaagc catatttttt   2324 tagggaaact aaggagtgac atagaactga tgaatgagta aaagtaagtt ttgctggatt   2384 tttgtagaac tctggacgtt gaggattcat tatgctgtgg ttaactttaa atatttttt   2442
```

<210> SEQ ID NO 2
<211> LENGTH: 255
<212> TYPE: PRT
<213> ORGANISM: Homo sapiens

<400> SEQUENCE: 2

```
Met Val Ile Ala Leu Leu Gly Val Trp Thr Ser Val Ala Val Trp
  1               5                  10                  15

Phe Asp Leu Val Asp Tyr Glu Glu Val Leu Gly Lys Leu Gly Ile Tyr
                 20                  25                  30

Asp Ala Asp Gly Asp Gly Asp Phe Asp Val Asp Asp Ala Lys Val Leu
             35                  40                  45

Leu Gly Leu Lys Glu Arg Ser Thr Ser Glu Pro Ala Val Pro Pro Glu
         50                  55                  60

Glu Ala Glu Pro His Thr Glu Pro Glu Glu Gln Val Pro Val Glu Ala
```

```
                65                  70                  75                  80
Glu Pro Gln Asn Ile Glu Asp Glu Ala Lys Glu Gln Ile Gln Ser Leu
                    85                  90                  95

Leu His Glu Met Val His Ala Glu His Val Glu Gly Glu Asp Leu Gln
                100                 105                 110

Gln Glu Asp Gly Pro Thr Gly Glu Pro Gln Gln Glu Asp Asp Glu Phe
                115                 120                 125

Leu Met Ala Thr Asp Val Asp Asp Arg Phe Glu Thr Leu Glu Leu Glu
        130                 135                 140

Val Ser His Glu Thr Glu His Ser Tyr His Val Glu Glu Thr Val
145                 150                 155                 160

Ser Gln Asp Cys Asn Gln Asp Met Glu Glu Met Met Ser Glu Gln Glu
                165                 170                 175

Asn Pro Asp Ser Ser Glu Pro Val Val Glu Asp Glu Arg Leu His His
                180                 185                 190

Asp Thr Asp Asp Val Thr Tyr Gln Val Tyr Glu Glu Gln Ala Val Tyr
            195                 200                 205

Glu Pro Leu Glu Asn Glu Gly Ile Glu Ile Thr Glu Val Thr Val Pro
        210                 215                 220

Pro Glu Asp Asn Pro Val Glu Asp Ser Gln Val Ile Val Glu Glu Val
225                 230                 235                 240

Ser Ile Phe Pro Val Glu Gln Gln Glu Val Pro Pro Asp Thr
                245                 250                 255

<210> SEQ ID NO 3
<211> LENGTH: 28
<212> TYPE: PRT
<213> ORGANISM: Cyprinus carpio

<400> SEQUENCE: 3

Val Lys Lys Ala Phe Ala Ile Ile Asp Gln Asp Lys Ser Gly Phe Ile
  1               5                  10                  15

Glu Glu Asp Glu Leu Lys Leu Phe Leu Gln Asn Phe
                20                  25

<210> SEQ ID NO 4
<211> LENGTH: 28
<212> TYPE: PRT
<213> ORGANISM: Oryctolagus cuniculus

<400> SEQUENCE: 4

Phe Lys Glu Ala Phe Ser Leu Phe Asp Lys Ala Gly Asp Gly Thr Ile
  1               5                  10                  15

Thr Thr Lys Glu Leu Gly Thr Val Met Arg Ser Leu
                20                  25

<210> SEQ ID NO 5
<211> LENGTH: 28
<212> TYPE: PRT
<213> ORGANISM: Meleagris gallopavo

<400> SEQUENCE: 5

Leu Ala Asp Cys Phe Arg Thr Phe Asp Lys Asn Ala Asp Gly Phe Ile
  1               5                  10                  15

Asp Ile Glu Glu Leu Gly Glu Ile Leu Arg Ala Thr
                20                  25

<210> SEQ ID NO 6
```

```
<211> LENGTH: 10
<212> TYPE: PRT
<213> ORGANISM: Homo sapiens

<400> SEQUENCE: 6

Ala Pro Pro Glu Asp Asn Pro Val Glu Asp
 1               5                   10

<210> SEQ ID NO 7
<211> LENGTH: 10
<212> TYPE: PRT
<213> ORGANISM: Homo sapiens

<400> SEQUENCE: 7

Glu Glu Gln Gln Glu Val Pro Pro Asp Thr
 1               5                   10

<210> SEQ ID NO 8
<211> LENGTH: 10
<212> TYPE: PRT
<213> ORGANISM: Homo sapiens

<400> SEQUENCE: 8

Asp Gly Pro Thr Gly Glu Pro Gln Gln Glu
 1               5                   10

<210> SEQ ID NO 9
<211> LENGTH: 11
<212> TYPE: PRT
<213> ORGANISM: Homo sapiens

<400> SEQUENCE: 9

Glu Gln Glu Asn Pro Asp Ser Ser Glu Pro Val
 1               5                   10

<210> SEQ ID NO 10
<211> LENGTH: 6
<212> TYPE: PRT
<213> ORGANISM: Homo sapiens

<400> SEQUENCE: 10

Pro Thr Gly Glu Pro Gln
 1               5
```

GENE ENCODING LABYRINTHIN, A MARKER FOR CANCER

This application is a divisional application U.S. Ser. No. 09/659,52 filed Sep. 12, 2000 U.S. Pat. No. 6,727,080), which is a continuation of PCT/US99/05365, filed Mar. 11, 1999, which is a continuation-in-part of U.S. Ser. No. 09/040,485 filed Mar. 17, 1998, now U.S. Pat. No. 6,166,176 issued Dec. 26, 2000.

The invention relates to a gene encoding a protein and peptides therefrom that includes an epitope, a cancer associated antigen, useful as a marker that is not restricted to previously defined histological classes of cancer. Antigenic peptides are useful as a vaccine for treatment and prevention of cancer. Antigenic peptides are useful as a vaccine for treatment and prevention of cancer, and for the preparation of new, specific, monoclonal antibodies. Antisense molecules are useful in pharmaceutical compositions and are useful for diagnosis and treatment.

BACKGROUND OF THE INVENTION

Cancer[1] is a leading cause of death in men and women throughout the world. In the United States alone, over 1 million new cases are diagnosed each year, and over 0.5 million deaths are reported annually (Landis et al., 1998). Historically, tumors are grouped and treated, based in part by the tissues in which they arise, e.g.—breast cancer, colon cancer, and lung cancer, and the like. Yet, within lung cancer, for example, it is well recognized that these tumors are a very heterogeneous group of neoplasms. This is also true for tumors arising in other tissues. In part, because of this heterogeneity, there are complex and inconsistent classification schemes which are used for human tumors. Previous attempts to treat cancer have been hampered by: 1) the arbitrary classification of tumors arising within given tissues, and 2) by using microscopic methods based on how these tumors look (histological classification). Although existing classifications for various tumor types have some prognostic value, almost all of the classifications fail to predict responsiveness to treatments and likelihood of cure or disease course. Improved classification schemes based on the biological constitution of these neoplasms is required to significantly alter the survival statistics of humans who have cancer. One approach to solving these problems is to locate molecules specific to tumors, preferably antigens in molecules that are markers for cancer cells. (A "marker" is defined herein as any property which can be used to distinguish cancer from normal tissues and from other disease states.) The markers' presence is then a basis for classification.

Terminology used herein is as follows, "cancer is a malignant tumor, wherein a "tumor" is an abnormal mass of tissue, that need not be malignant. "Neoplasm" us a form f new growth."

Monoclonal antibodies (MCAs) prepared by somatic cell hybridization techniques, usually in mice, are useful molecular probes for the detection and discrimination of cellular antigens, and therefore have great potential for detecting cancer associated antigens. These antibodies bind to specific antigens and the binding is detectable by well known methods. When binding occurs, the inference is made that a specific antigen is present. Those cancer associated antigens which are exposed to the cell surface or found in the cancer mass, are molecular targets for the immune systems (including host antibodies) of the host. Recent findings suggest that cancer patients who have antibodies against their tumors, do better than those who do not mount this type of immune response (Livingston, et al., 1994). Therefore, natural, induced, or administered antibodies are a promising therapeutic approach.

The humanization of non-human MCAs (the process by which non-human MCA reactive sites are shuttled into cloned human antibodies and expressed) results in reduced immunogenicity of the foreign antibodies without the loss of their specific binding in in vivo and in ex vivo applications. MCAs can be used as in vivo imaging agents diagnostic tests, and for therapy (Radosevich, et al. 1988, 1990; Rosen, et al. 1988).

Vaccine therapy is a well established approach directed at inducing an immune response without exposure to the causative agent of a disease or condition. Many vaccines are available, for example, to stimulate a response in a host to bacterial and viral agents. The use of tumor associated antigens (markers) in a vaccine could prevent primary cancer occurrence, and could also provide a means to prevent recurrence of the disease.

Gene therapy is a means by which the genetic make-up of cells is modified to express the gene of interest. There are many forms of gene therapy including: gene replacement, antisense suppression therapy, and surrogate gene expression. Discovering genes encoding cancer-associated, preferably cancer-specific antigens (markers) opens the door to genetic intervention against cancer cell proliferation. The accurate and consistent use of a cancer marker to differentiate cancerous from normal tissue, not only has diagnostic potential, but is also desirable for treatment and prognosis. Therefore, such markers have been sought.

Recent studies have shown that the enzyme encoding human aspartyl beta-hydroxylase (HAAH) is overexpressed in some human adenocarcinoma cell lines, and in primary hepatocellular cancers, therefore could be a marker. The gene said to encode HAAH has been cloned and sequenced (Gronke, et al., 1989, 1990; Wang, et al, 1991; Jia, et al., 1992, 1994; Korioth, et al., 1994; Lavaissiere, et al., 1996). However, little is known about HAAH expression in human tumors in general (Lavaissiere, et al., 1996).

The study of the HAAH enzyme grew out of the study of its bovine counterpart (Gronke, et al., 1989, 1990; Wang, et al., 1991; Jia, et al., 1992). Bovine aspartyl beta-hydroxylase is an intracellular, glycosylated protein, localized in the rough endoolasmic reticulum. The protein has been reported to have three major species of molecules; a 85 kilodalton form, and two active forms with molecular weights of 56 and 52 kilodaltons respectively (Lavaissiere, et al., 1996).

Using standard biochemical methods, bovine aspartyl beta-hydroxylase (bAAH) has been purified and characterized (Gronke, et al. 1990; Wang, et al., 1991). The activity of the enzyme has been shown to be correlated with the 52 and 56 kilodalton species which were purified. Immunologically, a related higher molecular weight form (85-90 kilodalton) was also observed. As part of the purification, bAAH is bound to Con A sepharose, which is consistent with the conclusion that the enzyme is glycosylated. (Subsequent reports on the DNA sequence show three possible glycosylation sites, with one site being very close to the known active enzyme domain.) The protein is very acidic in nature, and a detergent is not required to solubilize the active fraction. The active enzyme site is dependent from the biochemically isolated bovine protein (bAAH) on the presence of histidine at position 675 (Jia, et al., 1994).

A partial amino acid sequence was obtained for HAAH. DNA probes (a DNA probe is a molecule having a nucleotide sequence that is capable of binding to a specified nucleotide sequence under certain conditions) deduced from this amino acid sequence was used to screen a bovine cDNA library (Jia, et al., 1992). (A cDNA library contains the sections of DNA that encode for gene products, e.g. peptides as opposed to genomic DNA). Several overlapping cDNA sequences in the library contained a 764 amino acid open reading frame (ORF) sequence which will be expected to encode an 85 kilodalton protein. Also present in this ORF sequence were two other possible start codons, that is, locations at which encoding begins. The most 3' start codon was preceded by a ribosome binding site. Translation of the clone having this sequence resulted in a protein that was about 85 kilodaltons. Antiserum was raised to the membrane fraction of human MG-63 calls and was used to immuno-screen a cDNA library made from MG-63 cells. Data on one clone was reported which could encode a 757 amino acid protein, and, by sequence analysis, was found to have strong N-terminal homology with bAAH (Korioth, et al., 1994). When this clone was used in an in vitro translation system (an artificial cocktail of normal cell cytoplasm used to convert mRNA into protein), a 56 kilodalton protein was produced. It was suggested that this was due to posttranslational cleavage.

The HAAH enzyme is responsible for the modification of specific aspartic acid residues within the epidermal growth factor-like domains of proteins. It has been hypothesized that these modified aspartic acid residues allow the epidermal growth factor-like domains to become calcium binding domains. (Gronke, et al., 1989, 1990; Wang, et al., 1991; Jia, et al., 1992, 1994; Korioth, et al., 1994; Lavaissiere, et al., 1996).

An enzyme related to HAAH, aspartyl beta-hydroxylase (AAH), was first studied because it specifically modified select aspartic acid or asparagine residues in a group of biologically important proteins including the vitamin K-dependent coagulation factors VII, IX, and X. Other proteins like C, S, and Z also have this modification (Gronke, et al, 1989, 1990; Wang, et al., 1991; Jia, et al., 1992, 1994; Korioth, et al., 1994; Lavaissiere, et al., 1996). Aspartic acid and asparagine residues have been shown to be modified by HAAH in proteins containing epidermal growth factor-like domains. The function of the beta-hydroxyaspartic and beta-hydroxyasparagine residues is unknown, however, it has been speculated that this modification is required for calcium binding in the epidermal growth factor EGF-like domains of selected proteins.

Antibodies were raised to human hepatocellular carcinoma FOCUS cells (Lavaissiere, et al., 1990). One MCA reacted with an antigen that was highly expressed in hepatocellular carcinomas (Lavaissiere, et al., 1996). Immunoscreening using this antibody and a lambda gt11 HepG2 library resulted in the isolation of a partial cDNA, which was subsequently used to isolate a larger clone.

A human adenocarcinoma cell line designated A549 was reported as having very high levels of HAAH activity (Lavaissiere, et al., 1996). A mouse monoclonal antibody designated MCA 44-3A6 (U.S. Pat. No. 4,816,402) was produced against the human adenocarcinoma cell line A549 (ATCC accession number CCL 185) (Radosevich, et al., 1985). The antibody recognized a cell surface, non-glycosylated antigenic protein having an estimated apparent molecular weight of 40 kDa.

The antigen was expressed by A549 cells, and was found to be a good adenocarcinoma marker; that is, it was frequently expressed by cancers which looked like adenocarcinomas when examined histologically (Radosevich, et al., 1990a; Lee, at al., 1985). MCA 44-3A6 is unique in that it is the first monoclonal antibody which has this binding specificity. The results from an International Workshop for Lung cancer confirmed other related published findings on MCA 44-3A6 (Stahel, 1994).

The antibody designated MCA 44-3A6 has clinical utility because it differentiates antigens associated with adenocarcinomas. The normal and fetal tissue distribution of the antigen is restricted to some glandular tissues (Radosevich, et al., 1991). Detection can occur on formalin fixed-paraffin embedded tissue (Radosevich, et al., 1985, 1988, 1990a, 1990b; Lee, et al., 1985, 1986; Piehl, et a. 1988; Combs, et al., 1988b, 1988c; Banner, et al., 1985). The antibody has a restricted binding pattern within human pulmonary tumors (Lee, et al., 1985; Banner, et al., 1985; Radosevich, et al., 1990a, 1990b).

In a study of over two hundred pulmonary cancers, MCA 44-3A6 was found to react with all of the adenocarcinomas tested, many of the large cell carcinomas, as well as with subsets of intermediate neuroendocrine small cell lung cancers, well-differentiated neuroendocrine small cell carcinomas, carcinoids, but not mesotheliomas. MCA 44-3A6 does not react with squamous cell carcinoma, bronchioloalveolar carcinoma, or small cell carcinoma (Lee, et al., 1985). MCA 44-3A6 is useful in distinguishing adenocarcinomas that are metastatic to the pleura from mesothelioma (Lee, et al., 1986). The antibody has selected reactivity among adenocarcinomas and in large cell carcinomas (Piehl, et al., 1988; Radosevich, et al., 1990b).

In a study of over 40 cases of lung cancer comparing cytological and histological findings, MCA 44-3A6 was found to be useful in cytological diagnosis and was consistent with the histological finding (Banner, et al., 1985). Histology is the study of tissues (which are made of cells). Cytology is the sturdy of cells which have been removed from the organizational context which is commonly referred to as tissue. Cells removed from tissues do not always behave the same as if they were in the tissue from which they were derived. Fortunately, the antigen detected by MCA 44-3A6 expressed in adenocarcinoma cells in tissue behaves in the same ways as adenocarcinoma cells removed from tissues. This is a very diagnostically important characteristic. Similar correlations using cytologically prepared cell blocks of pulmonary carcinomas, as well as ACs presenting in body fluids from other sites throughout the body were demonstrated (Lee, et al., 1985; Spagnolo, et al., 1991; Combs, et al:, 1988c). Also, MCA 44-3A6 binds to adenocarcinomas from sites other than lung cancer. The expression of the antigen in primary and metastatic lesions was also reported (Combs, et al., 1988a). The utility of the MCA antibody in differentiating cancer from benign lesions in human breast tissue was also noted (Duda, et al., 1991).

The cellular localization of the antigen detected by MCA 44-3A6 W2s determined. By using live cell radioimmunoassays (a radioactive antibody test directed at determining binding of the antibody to live cells), immunofluorescence, and live cell fluorescence activated cell sorter (FACS) analysis, the antigen detected by MCA 44-3A6, was shown to be on the outside surface of the cell (Radosevich, et al., 1985). Additional studies using immunogold-electron microscopy and FACS analysis have demonstrated that this antigen is non-modulated (that is not internalized by the cancer cell when bound by an antibody), is expressed on the extracellular surface of the plasma membrane, and is not cell cycle specific that is, the cell makes protein all the time it is going through the process of cell replication, and also when it is not dividing (Radosevich, et al., 1991). The antigen is not found in the serum of normal or tumor bearing patients, and is not shed into the culture media by positive cell lines (that is, cancer cells are known to bleb off portions of their cell membranes and release them into the surrounding fluid.) (Radosevich, et al., 1985). Recently 3 of 27 randomly tested adenocarcinoma patients were found to have naturally occurring antibodies to the antigen. In addition, radiolabeled MCA 44-3A6 was used to localize A549 tumors growing in nude mice. A douxorubicin immunoconjugate MCA 44-3A6 is selectively toxic in vitro (Sinkule, et al., 1991).

Determination of the nucleotide and amino acid sequences of the antigen detected by MCA 44-3A6 would enhance the usefulness of this antigen in cancer diagnosis, treatment and prevention.

BRIEF SUMMARY OF THE INVENTION

The antigen detected by the antibody MCA 44-3A6 as described in the Background is now designated as "Labyrinthin." A gene (designated labyrinthin; abbreviated lab) characterized by a unique nucleotide sequence that encodes the antigen detected by MCA 44-3A6 was isolated and characterized. (lab notation signifies the nucleic DNA/RNA forms; "Lab" notation refers to the protein which is encoded by the lab DNA/RNA).

The invention described herein used the antibody MCA 44-3A6 as a tool to clone the gene encoding Lab. In addition, an epitope (the necessary binding site for an antibody found on the antigen) for MCA 44-3A6 was identified on the Lab protein expressed by the clone to be PTGEPQ[2] (SEQ ID No: 10). The epitope represents an important immunodominent sequence; that is, when injected into animals, the animals readily produce antibodies to this sequence.

[2] Standard abbreviations for amino acids.

An aspect of the invention is the use of lab DNA in the sense[3], expression mode for: 1) the marking of human tumors by nucleotide probes; 2) the detection of DNA and mRNA expression of lab in cells and tissues; 3) the transformation of cells into a glandular-like cell type; 4) the production of Lab antigen in vivo for immunization; 5) the ex vivo expression of Lab for immunization to produce antibodies; and 6) production of Lab in vitro. Use of an antisense molecule, e.g. by production of a mRNA or DNA strand in the reverse orientation to a sense molecule, to suppress the growth of labyrinthin-expressing (cancerous) cells is another aspect of the invention.

[3] The normal transcription of a DNA sequence which proceeds from the 3' to the 5' end to produce a mRNA strand from the sense strand of DNA, the mRNA being complementary to the DNA.

An aspect of the invention is a vector comprising a DNA molecule with a nucleotide sequence encoding at least an epitope of the Lab antigen, and suitable regulatory sequences to allow expression in a host cell.

Another aspect of the invention is an amino acid sequence deduced from the protein coding region of the lab gene. Selected regions of the sequence were found via immunological methods, to produce effects corresponding to effects from both naturally occurring (from cancer cells), chemically produced (synthetically produced peptides), and expression products of the cloned lab gene.

Another aspect of the invention is the use of the entire deduced amino acid sequence of Lab, peptides derived from Lab, or chemically produced (synthetic) Lab peptides, or any combination of these molecules, for use in the preparation of vaccines to prevent human cancers and/or to treat humans with cancer. For purposes of the present invention, "humans with cancer" are those persons who have the Lab antigen detected in their cells. These preparations may also be used to prevent patients from ever having these tumors prior to their first occurrence.

Monoclonal antibodies directed to the Lab protein, or antigenic components or derivatives of Lab proteins, are useful for detection of Lab and for other purposes. Monoclonal antibodies which are made in species other than those which react with the Lab antigen can be modified by a number of molecular cloning methods such that they retain their binding with the Labyrinthin peptides, yet are not immunogenic in humans (Sastry, et al., 1989; Sambrook, et al., 1990). In brief, this is done by replacing the binding site sequence of a cloned human antibody gene, with the binding site sequence of the non-human monoclonal antibody of interest. These "humanized" MCAs are used as therapeutic and diagnostic reagents, in vivo, ex vivo, and in vitro.

The use of the Lab protein or antigenic peptides derived therefrom in diagnostic assays for cancer is a way to monitor patients for the presence and amount of antibody that they have in their blood or other body fluids or tissue. This detection is not limited to cancers of a class or classes previously defined, but is useful for cancer cells that have the Lab marker antigen. The degree of seroconversion, as measured by techniques known to those of skill in the art [e.g., ELISA (Engrall and Perimann, 1971)] may be used to monitor treatment effects.

Treatment with antisense molecules to lab or antibodies to Lab in a pharmaceutical composition is an approach to treat patients who have Lab in, or on, their cancer cells.

BRIEF DESCRIPTION OF THE DRAWINGS

FIG. 1 is the nucleic acid sequence of the lab gene.

FIG. 2 is the amino acid sequence for Lab, deduced from the lab gene.

FIG. 3 is an illustration of the lab gene and how it is related to the HAAH enzyme.

DETAILED DESCRIPTION OF THE INVENTION

Molecular Biology of Labyrinthin: To demonstrate that the epitope MCA 44-3A6 is encoded by a protein sequence, high molecular weight DNA from the cell line A549 was isolated. This DNA was co-precipitated (via calcium) with a plasmid (pSVneo), and used to transfect a mouse cell line designated B78H1 cells (Albino, et al., 1985). This mouse cell line is negative for the expression of the epitope and was reported to have a high frequency of incorporation and expression of any human DNA sequences. If a given B78H1 cell was in a state to take up DNA, it would be expected to have taken up both human DNA and the plasmid DNA. The plasmid DNA makes the cell resistant to G418 (a normally toxic drug). Therefore, if a cell normally sensitive to G418 growth inhibitor grows in G418, it had to have taken up the plasmid, and may also have taken up one or more A549 DNA sequences. After G418 selection (a way of choosing only cells which have resistance to growth in G418 by the uptake/expression of the Neo gene on pSVneo plasmid, and therefore representing cells that were in a state to uptake other DNA at the same time), approximately 15 of $1 \times 10^5$ clones were detected using immunoselection with MCA 44-3A6. This finding is consistent with a conclusion that human A549 cells have DNA that encodes Lab and possesses the regulatory sequences necessary for the expression of Lab.

Comparison of HAAH and Labyrinthin: Because the DNA sequence of lab was determined as an aspect of the present invention, HAAH and lab could be compared. HAAH and the lab nucleotide sequences have some internal fragment similarities, but are different on either side of the fragment, and are related to different products. This conclusion is based in part by the analysis and homology of the DNA sequences reported for these two genes. Specifically, the lab 5' region has no homology with HAAH. The protein coding region of lab has about a 99.6% homology with an internal segment of the proposed protein coding region for HAAH. The 3' region has no homology with the HAAH reported sequence. Virtually all of the other data comparing HAAH and labyrinthin are different, for example: 1) molecular weights of the proteins, 2) cellular localization, 3) chromosome localization, 4) histological presentation in normal tissues and tumors, 5) northern blot expression, 6) immunological findings.

Although the protein coding region of lab is identical to an internal region of the sequence reported for HAAH, the 5' untranslated region of HAAH is different, and part of the 5' translated protein coding region of HAAH is missing from that found in the lab clone. From both HAAH and lab clones, the deduced protein would be expected to be very acidic in nature, and therefore would run anomolously in SDS gels. As predicted, the Lab protein migrates anomolously in SDS gels. What was cloned and disclosed in the present invention migrates identically to the native protein found in several cell lines. Convincing evidence that the correct gene fragment encoding the antigen detected by MCA 44-3A6 has been cloned (mRNA) is that when the recombinant protein is made, that recombinant protein should act (in this case—have an apparent molecular weight) the same as independent biologically derived source of that protein. Lab provided from clones has the characteristics of Lab from cells.

The deduced amino acid sequence encoded by HAAH requires the use of an open reading frame which would produce a protein that is 85-90 kilodaltons, and does not take into account that there are several start codons and other shorter open reading frames. The deduced HAAH protein (biochemically) is glycosylated and the reported sequence has glycosylation sites (Korioth, et al., 1994; Lavaisslere, et al., 1996). To the contrary, Lab is not glycosylated, nor does it have predicted glycosylated sites.

The deduced HAAH amino acid sequence contains a region shared by the Lab amino acid sequence which is predicted to be very hydrophobic. Lab requires strong detergents in order to be soluble; HAAH does not. The increased expression of HAAH (by enzyme activity measurements) in the same cell line (A549) which was used to clone and study lab extensively, suggests that both of these gene products may be important to the AC phenotype and that at least A549 cells make both functional HAAH and Lab. Successful transfections of the antisense to lab into A549 resulted in a marked decrease in expression of lab and in the growth rate of the cells. The expression of a sense lab construct in NIH-3T3 cells (normal mouse fibroblasts) resulted in a marked change in phenotype, a phenotype consistent with that of ACs. Therefore, lab expression is associated with conversion of normal cells to cancerous cells. Lab and HAAH have potential calcium binding domains in common.

cDNA Library Contruction and Cloning: A cDNA lambda gt11 phage library was constructed using mRNA which was isolated from actively growing A549 cells (Sambrook, et al., 1990). This oligo(dT)-primed cDNA was cloned into the Eco RI site using Eco RI linkers. The library has about 83% clear (containing an insert) plaques with a titer of $1.2 \times 10^{10}$/ml representing a minimum of $1.46 \times 10^6$ independent plaques which, by Polymerase Chain Reaction, have insert sizes ranging from 0.6 to 5 kilobases. Since Lab is a 40 kilodalton integral protein, (a protein which is embedded in the plasma membrane) the theoretical full length mRNA encoding this protein, including a potential leader sequence is estimated to be about 1.1 kilobases. This library was immunoscreened using the antibody MCA 44-3A6. Eight independently derived phage stocks (identical phage which are from the same plaque) were isolated. These have all been plaque purified by repeated cycles of immunoscreening/isolation. Upon Eco RI digestion of these eight isolates, inserts of about 2 kb were seen. The largest insert was isolated (2A1A1) and the Eco RI fragment was cloned into the pGEM-3Z plasmid.

Sequencing and Sequence Analysis: The DNA fragment designated 2A1A1 was found to have an insert of 2442 base pairs in length (FIG. 1), containing a 5' untranslated region, a ribosome binding site, and a start codon which would be expected to encode a 255 amino acid protein (FIG. 2). The 3' untranslated region is remarkable in that it contains only four instability sequences; ATTTA (Xu, et al., 1997). In addition there are sequences found in the very 3' end of mRNA's which result in adenylation of the mRNA (Sambrook, et al., 1990). The lab sequence contains both a sub-optimal (ATTAAA) and optimal (AATAAA) poly-adenylation site. These are sequences found in the very 3' end of mRNA's which result in adenylatlon of the mRNA. This finding provides molecular data which supports the cellular and biochemical data that has been outlined herein. (The HAAH clone has a poly A signal, but the whole 3' region has not been sequenced.)

A calcium binding site motif is noted in the Lab amino acid sequence (FIG. 2), however, it is out of the known required structural context to be a binding site. In this case, the calcium limiting sequence is there, but it is not in a protein sequence context that is known to make it work as a binding site. Homology was noted with lab and an EST clone (designated #055501) which represented only a portion of the 3' untranslated region and independently confirmed this portion of the sequence. Some internal fragment homology is also noted with HAAH, but the 5' untranslated and part of the 5' translated region is different (58 amino acids), as well as a major portion of the 3' coding region is missing in lab FIG. 3).

Genomic DNA Cloning and Analysis: Using a PCR fragment representing the protein coding region of lab as a probe, a genomic lambda FIX II library made from the human pulmonary fibroblast cell line WI-38 was screened. Ten primary plaques were isolated out of approximately $1 \times 10^6$ screened plaques. Using seven of these as target DNA, Polymerase Chain Reaction conditions were established with primers for the protein coding region, producing a 765 base pair fragment, the expected protein coding region for lab. On Northern blots (a method used to qualitatively assess mRNA) lab only detects one band noted at 2.7 kilobases. The recombinant protein made from the lab clone, when tested on Western blots (a method used to qualitatively define proteins) using MCA 44-3A6, has the same relative mobility as the Lab protein when made by A549 cells.

Lab and HAAH genes give different results in the proteins they encode. HAAH consistently gives two bands on Northern blot analysis (2.6 and 4.3 kilobases) suggesting that the 2.6 kilobase band is due to alternative splicing, i.e. the cell cuts and splices the mRNA. Also, if lab and HAAH are the same gene, HAAH should be detected in all tissues and cancer cell lines in which Lab is found. However, Lab is not seen on Northern blots of cell lines EMT6 or QU-DB, nor is there immunoreactivity in these cells; indicating that Lab mRNA is not made, and that Lab protein is not produced in these cells. Lab protein is rarely expressed in normal cells, where both the HAAH mRNA and HAAH protein have been reported to be expressed in almost every tissue studied.

mRNA Analysis: Northern blot analysis of the DNA fragment from the A549 cell line using lab cDNA as a probe identified a single band of about 2.7 kilobases. This is expected based on the cDNA (2442 base pairs) and a poly-A tail of about 300 base pairs. Northern blot analysis of the mouse cell line, EMT6, and of the human large cell carcinoma cell line, QU-DB, confirm that no transcript for lab is produced by these cells. This is consistent with immunoassays which are negative for lab expression on these cells.

Antisense and Sense cDNA Expression. The plasmid (pBK-CMV) (Sambrook, et al., 1990) may carry either the sense or antisense full length cDNA lab into A549 and NIH 3T3 cells. An antisense molecule can be, for example, a complementary sequence to a sense molecule that hybridizes with the sense molecule, preventing its expression. Using the MTT assay (Siddique, et al., 1992) to assess the growth rate of A549 cells expressing antisense to lab, a marked reduction in growth rate was noted. The antisense transfected A549 cells appear to have a greater degree of contact inhibition. A detectable amount of Lab is reduced in these antisense transfected cells. NIH-3T3 cells convert from a fibroblast-like cell type morphology (large, thin spindle shaped) to a large, adenocarcinoma appearing cells (very round, plump) when sense expression occurs.

Chromosome Localization: The chromosome localization for lab, using full length cDNA as a probe via in situ hybridization (Sambrook, et al. 1990) is tentatively on chromosome 2q12-14, with possibly some reactivity to chromosomes 4 and 8. Using the same probe (the full length cDNA sequence of lab) and FACS sorted chromosomes (Lebo, et al. 1985) staining was also noted on chromosome 2, with weak staining on 4 and none on 8. The use of genomic clones will be of particular value in resolving these data because higher stringency hybridization conditions than that allowable for the cDNA, can be used, thereby reducing background signals. This is yet another proof that the correct gene was cloned and that the results are not due to a method artifact. There may be mutations in the genomic DNA of tumors and for the present invention, DNA was cloned from tumor cells (A549). Therefore, a mutated gene could have been cloned. However, that is not the case because the genomic DNA from a normal cell (DNA) produced the same sequence as what cloned as described herein. Therefore, a normal gene was cloned from A549 cells. The weak signals on chromosomes 4 and 8 are consistent with a pseudogene or a related gene. For example, HAAH has been reported to be on chromosome 8q12 by in situ hybridization, so this result on chromosome 8 could reflect the HAAH and lab sequence homology.

Protein Molecular Characterization of Labyrinthin: Previous work using Western blot analysis (a qualitative assay to assess antigens) has shown that the Lab antigen is a 40 kilodalton (by relative mobility) protein detectable in A549 cells (Radosevich, et al., 1985). The epitope does not appear to be modulated or blocked by lectins, and is selectively expressed on the cell surface, primarily localized to the plasma membrane. (Radosevich, et al., 1985, 1991). Lab is sensitive to proteases, but not lipid or carbohydrate altering reactions (Radosevich, et al., 1985). The biochemical properties of Lab are consistent with Lab being an integral membrane protein.

Having a deduced amino acid sequence from the lab gene of the present invention, allows further characterization of the Lab protein. Extensive computer analysis of Lab has identified a eukaryotic leader-like sequence and theoretical cleavage site, 3 myristylation sequence sites, a weak membrane anchoring domain (MAD I), and a strong membrane anchoring domain (MAD II) (FIG. 2). [(In the HAAH sequence, there are 58 (theoretical) amino acids followed by a sequence homology in the Lab protein coding sequence and an additional 445 amino acid 3' to the lab sequence.)]

When Lab is expressed as a fusion protein in a bacterial GST fusion expression system (pGEMEX-2T) (Amereham Pharmacia Biotech, Inc., Piscataway, N.J., 08854, USA), and subjected to Western blot analysis using the antibody MCA 44-3A6, the resulting blots demonstrate that the expressed cleaved fusion protein has the same relative mobility as the protein detected in A549 cells. The deduced molecular weight for Lab is 28.8 kilodaltons and on Western blots it has a relative mobility identical to the form expressed by A549 cells (apparent relative mobility=40 kilodaltons). The 55 glutamic and 27 aspartic acid residues a (82 residues combined) are almost uniformly distributed throughout the protein (255 amino acids total; 228 no leader sequence), except for the leader sequence and the strongest membrane anchoring domain (MAD II). These data suggest that Lab migrates anomelously in SDS gels. Cell lines other than A549 (e.g. adenocarcinomas DU-145, ATCC # HTB-81; ZR-75-1, ATCC # CRL-1504, and so forth) have an antigen detected with the same molecular weight antigen as Lab. Neither a 85-90 kilodalton molecular weight species, nor a 52 and 56 kilodalton molecular weight species is noted when probing Western blots for Lab.

Epitope Mapping Using the Antibody MCA 44-3A6 and Vaccine Feasibility of Lab: Using Polymerase Chain Reaction and the GST fusion protein system, subclones of the protein coding region were made, and epitopes mapped the binding of MCA 44-3A6 to six amino acids (PTGEPQ). (SEQ ID NO: 10) representing amino acids #117-122 of Lab ("P" peptide). In order to determine this epitope, the entire coding region was divided into regions, Polymerase Chain Reaction primers were designed to amplify each region, and the subsequent expression of Polymerase Chain Reaction products were cloned and tested by Western blot analysis using the antibody MCA 44-3A6.

The DNA fragment representing the positive Western blot result was then further subdivided. Polymerase Chain Reaction products were generated and cloned, expressed, and tested via Western blot. Constructs were made in this way both from the 5' end and the 3' end and the intervals of the number of amino acids were reduced upon each round. This resulted in the last round representing a one amino acid difference from the previous round (in both directions), such that one could deduce the exact binding site of the MCA 44-3A6. This demonstrates that at least these six amino acids are exposed to the external cell surface. To further prove the point, the DNA encoding only these six amino acids have been cloned and the fusion protein is positive by Western blot analysis. Synthetically prepared "P" peptide can be specifically detected by MCA 44-3A6, and the synthetic peptide was immunogenic in 5 of 5 mice tested. Computer analysis/modelling also predicted that this epitope would be very immunogenic using computer assisted analysis (GCG programs) (Genetics Computer Group, Madison, Wis. 53703).

Vaccine Preparation: A vaccine is a preparation of antigen(s), which when given to a host, results in the host producing antibodies against the antigen(s). The host response results in the host being immune to the disease to which the vaccine was directed. Vaccine treatment therefore, prevents the clinical presentation of a disease, without the host being exposed to the disease causing agents. Lab has all the characteristics of a preferred cancer vaccine. The lab gene is frequently expressed by tumors which look like adenocarcinomas, is expressed an the outside of the cells, is expressed by all of the cells within a given S cancer, is expressed at all times by these cancer cells, and is infrequently expressed by normal cells. Lab protein (peptides) can be produced by any number of methods using molecular cloning techniques, and can be produced in large quantities, thus making it a practical antigen to use as a vaccine. After the Lab protein has been purified so that it is suitable for injection into humans, it is administered to individuals intradermally, subcutaneously, or by other routes, so as to challenge the immune system to produce antibodies against this protein (peptides).

The use of molecular modeling and computer assisted analysis GCG programs (Genetics Crystal Group, Madison, Wis. 53703) allows the identification of small portions of a molecule, slightly larger than an epitope (six to seven amino acids for proteins), which are expected to be on the surface of a protein molecule. In addition, the degree of hydrophobicity or hydrophilicity of a given sequence, and how immunogenic the sequence would be in animals, can be determined (Genetics Crystal Group, Madison, Wis. 53703). After defining which sequences meet these criteria, the peptides are synthetically made, or produced by a number of standard methods. One or more of these peptides can then be formulated to be used as a vaccine, and administered to the host as outlined above, as a vaccine.

A vaccine comprising a molecule having an amino acid sequence selected from the group of sequences encoded by the cDNA of FIG. 1, sequences of FIG. 2, encoded by the cDNA, the peptides APPEDNPVED, (SEQ ID NO:6), EEQQEVPPDT, (SEQ ID NO:7), DGPTGEPQQE (SEQ ID NO:8), and EQENPDSSEPV (SEQ ID NO:9), and any fragments or combinations thereof.

A given vaccine may be administered once to a host, or may be administered many times. In order for some patients to recognize a given vaccine, an adjunct may also need to be administered with the peptides. Adjuvants are nonspecific immune stimulators which heighten the immune readiness and aid in the conversion of the host from not having detectable serum antibodies to having very high titer serum antibodies. It is this high level (titer) of antibodies, which effectively protects the host from the diseases or conditions to which the antibodies are directed, Functional Studies: Studies directed at understanding the cellular function(s) of Lab are extensions of cell localization/characterization studies (Siddique, et al., 1992). Changes in levels of Lab in response to extracellular exposure to various response to extracellular exposure to various cations ($Ca^{++}$, $Mg^{++}$, $Cu^{++}$, and $Fe^{++}$) were undertaken. Lab expression in A549 cells was only modulated by $Ca^{++}$. Using the highly specific fluorescent Fura-2/AM $Ca^{++}$ method of measuring cytosolic $Ca^{++}$, (Molecular Probes Inc., Eugene, Oreg. 97402) it was demonstrated that; 1) the internal $Ca^{++}$ concentration is higher in A549 cells than in QU-DB cells, and 2) that the A549 cell line responds to various external $Ca^{++}$ levels (Siddique, et al., 1992). Since pH can modulate intracellular free $Ca^{++}$ levels, external pH manipulations should result in changes in the expression levels of Lab. Extracellular pH changes (in the presence of normal $Ca^{++}$ concentrations) result in 1) a parallel change in intracellular pH as measured by SNARF-1 AM/FACS, (Molecular Probes Inc., Eugene, Oreg. 97402) 2) transcript levels increase for Lab (when compared to GAPDH expression via Northern blot); and that 3) Lab protein also increases (using Western/Slot blot analysis). The intracellular changes in pH (due to external changes) for A549 cells are Identical to those reported for normal cells. The increased expression of lab is also not due to cell death (as measured by MTT assays) (Siddique, et al., 1992). In addition, incubation of recombinant Lab at various pH solutions does not alter immunoreactivity. Preliminary data suggests that when these experiments are conducted on A549 cells grown in reduced $Ca^{++}$, the induced expression of lab is blunted.

Methods of Diagnosing Cancer Cells in a Sample of Cells: Biological samples from a subject are used to determine whether cancer cells are present in the subject. Examples of suitable samples include blood and biopsy material. One method of diagnosis is to expose DNA from cells in the sample to a labeled probe that is capable of hybridizing to the lab gene, or a fragment thereof, under stringent conditions, e.g. 6×ssc; 0.05× blotto; 50% formamide; 42° C. (Sambrook, et al., 1990). Of course, the hybridizing conditions are altered to achieve optimum sensitivity and specificity depending on the nature of the biological sample, type of cancer, method of probe preparation, and method of tissue preparation.

After contacting the sample with the probe, the next step is determining whether the probe has hybridized with nucleotide sequences of the DNA from the sample, from which the presence of the lab gene is inferred, said presence being diagnostic of cancer.

Another diagnostic method is to obtain monoclonal antibodies preferably labeled, either antibodies already existing, or new ones directed to the antigenic peptides that are aspects of the present invention, and contact a sample with these to detect the Lab antigen. These monoclonal antibodies are useful in the development of very specific assays for the detection of Lab antigen, and allow the tests to be carried out in many different formats; resulting in a broader application in science and medicine.

The current invention is useful in that it describes a new gene which is expressed on the surface of tumors, which was not previously reported. This gene is not tissue specific, and therefore will allow the detection of tumors regardless of the organ in which they arise. Likewise, the use of this gene to produce a vaccine for these tumors, will have a very broad application. Diagnostic tests will also have this broad tissue use, making the detection of Lab/lab a "pan-marker" for cancer, in particular for what have been designated previously, adenocarcinomas.

DOCUMENTS CITED

Albino, A P, Graf, L H, Kontor, R R S, et al. DNA-mediated transfer of human melanoma cell surface glycoprotein gp130: Identification of transfectants by erythrocyte resetting. Mol. Cell. Biol. 5:692-697, 1985.

Banner B F, Gould V E, Radosevich J A, et al. Application of monoclonal antibody 44-3A6 in the cytodiagnosis and classification of pulmonary carcinomas. Diag Cytopathol. 1:300-307, 1985.

Brown, D T and Moore, M. Monoclonal antibodies against two human lung carcinoma cell link. Br. J. Can. 46:794-801, 1980.

Combs S G, Hidvegi D F, Ma Y, et al. Pleomorphic Carcinoma of the Pancreas: A rare case report of combined histological features of pleomorphic adenocarcinoma and giant cell tumor of the pancreas. Diag. Cytopathol. 4:316-322, 1988a.

Combs S G, Radosevich J A, Ma Y, et al. Expression of the Antigenic Determinant Recognized by the Monoclonal Antibody 44-3A6 on Select Human Adenocarcinomas and Normal Human Tissues. Tumor Biol. 9:116-122, 1988b.

Combs S G, Radosevich J A, and S T Rosen. Cytological expression of the adenocarcinoma antigen marker in human body fluids. Tumor Biol. 9:116-122, 1988c.

Duda R B, August C Z, Radosevich J A and S T Rosen. Monoclonal Antibody 44-3A6 as a Marker For Differentiation of Breast Cancer. Tumor Biol. 12:254-260, 1992.

Engvall, E and Perlmann, P. Enzyme linked immunosorbent assay (ELISA): Quantitative assay of IgG. Immunochemistry. 8:87-874, 1971.

Gronke R S, VanDusen W J, Garsky V M, Jacobs J W, Sardana M K, Stern A M, and P A Friedman. Aspartyl beta hydroxylase: In vitro hydroxylation of a synthetic peptide based on the structure of the first growth factor-like domain of human factor IX. PNAS. 86:3609-3613, 1989.

Gronke R S, Welsch D J, VanDusen W J, Garsky V M, Sardana M K, Stern A M, and P A Friedman. Partial purification and characterization of bovine liver aspartyl beta hydroxylase. J. Biol. Chem. 265:8558-8565, 1990.

Jia S, VanDusen W J, Diehl R E, Kohl N E, Dixon R A F, Elliston K O, Stern A M, and P A Friedman. cDNA cloning and expression of bovine aspartyl (asparageinyl) beta-hydroxylase. J. Biol. Chem. 267:14322-14327, 1992.

Jia S, McGinns K, VanDusen W J, Burke C J, Kuo A, Griffin P R, Sardana M K, Elliston K O, Stern A M, and P A Friedman. A fully active catalytic domain of bovine aspartyl (asparaginyl) beta-hydroxylase expressed in *Escherichia coli*: Characterization and evidence for the identification of an active-site region in vertebrate alpha-ketoglutarate-dependent dioxygenases. PNAS 91:7227-7231, 1994.

Korioth F, Gieffers C, and J Frey. Cloning and characterization of the human gene encoding aspartyl beta-hydroxylase. Gene 150:395-399, 1994.

Landis, S. H., Murray, T., Bolden S., and P. A. Wingo. Cancer Statistics, 1998., CA 44:6-9.

Lavaissiere L, Jia S, Nishiyama M, de la Monte S, Stren A M, Wands J R, and P A Friedman. Overexpression of human aspartyl (asparaginyl) beta-hydroxylase in hepatocellular carcinoma and cholangiocarcinoma. J. Clin. Invest. 98:1313-1323, 1996.

Lebo, R V, Tolan, D R, Bruce, B D, Cheng, M C, and Kan, Y W. Spot blot analysis of sorted chromosomes assigns a fructose intolerance gene locus to chromosome 9. Cytometry. 6:476-483, 1985.

Lee I, Radosevich, J A, Rosen, S T, et al. Immunohistochemistry of lung carcinomas using monoclonal antibody 44-3A6. Can. Res. 45:5813-5817, 1985.

Lee I, Radosavich J A, Chajfeo G, et al., Mallgnant Mesothellomas: Improved Differential Diagnosis From Lung Adenocarcinomas Using Monoclonal Antibodies 44-3A6 and 624A12. Amer. J. Path. 123:497-507, 1986.

Livingston, P O, Wong, G Y C, Adluri, S, Tao, Y, Padevan, M, Parente, R, Hanlon, C, Calves, M J, Helling, F, Ritter, G, Oettgen, H F, and Old, L J. Improved survival in AJCC stage III melanoma patients with GM2 antibodies: A randomized trial of adjuvant vaccination with GM2 ganglioside. J. Clin. Oncol., 12:1036-1044,1994.

Piehl M R, Gould V E, Radosevich J A, et al. Immunchistochemical Identification of Exocrine and Neuroendocrine Subsets of Large Cell Lung Carcinomas. Path. Res. and Prac. 183:675-682, 1988.

Radosevich J A, Ma Y, Lee I, et al. Monoclonal antibody 44-3A6 as a probe for a novel antigen found human lung carcinomas with glandular differentiation. Can. Res 45:5805-5812, 1985.

Radosevich J A, Lee I, Gould V E, and S T Rosen. Monoclonal antibody assays for lung cancer. In: In vitro diagnosis of human tumors using monoclonal antibodies. Kupchik H Z and N Rose (Eds.) Marcel Dekker p101-119, 1988.

Radosevich J A, Combs S G, and S T Rosen. Immunohistochemical analysis of lung cancer differentiation markers. In: Lung Cancer Differentiation. Lung Biology in Health and disease. L'Enfant C, Bernal S, and Baylin S. (Eds.). Marcel Dekker, 1990a.

Radosevich J A, Noguchi M, Rosen S T, Y. Shimosato. Immunocytochemical analysis of human adenocarcinomas and bronchioloalveolar carcinomas of the lung using the monoclonal antibody 44-3A6. Tumor Biology. 11:181-188, 1990b.

Radosevich J A, Combs S G, and S T Rosen. Expression of MCA 44-3A6 in human fetal development. Tumor Biology 12:321-329, 1991.

Radosevich J A, Siddique F S, Rosen S T, and W J Kabat. Cell Cycle and E M Evaluation of the Adenocarcinoma Antigen Recognized by the Monoclonal Antibody 44-3A6. Br. J. Can. 63:86-87, 1991.

Rosen, S T, Mulshine, J L. Cuttitta, F, and Abrams, P G. Biology of Lung Cancer. Marcel Dekker, Inc. New York, N.Y., Vol. 37, 1988.

Sambrook J, Fritsch E F, and T Maniatis. Molecular cloning: a laboratory manual. 2nd Ed. Cold Spring Harbor Lab. Press., 1990.

Sastry, L., Alting-Mees, M, Huse, W D, Short, J M, Hay, B N, Janda, K D, Benkovis, S J, and Lerner. Cloning of the immunological repertoire in *Escherichia coli* for generation of monoclonal catalytic antibodies: Construction of a heavy chain variable region-specific cDNA library. PNAS. 86:5728-5732, 1989.

Siddique F S, Iqbal Z, and J A Radosevich. Changes in the expression of the tumor-associated Antigen recognized by monoclonal antibody 44-3A6 in A549 cells due to calcium. Tumor Biol. 13:142-151, 1992.

Sinkule J, Rosen S T, and J A Radosevich. MCA 44-3A6 Douxorubicin (Adriamycin) Immunoconjugates: Comparative In Vitro Anti-Tumor Efficacy of Different Conjugation Methods. Tumor Biol. 12:198-206, 1991.

Spagnolo D V, Witaker D, Carrello S, et al. The use of monoclonal antibody 44-3A6 in cell blocks in the diagnosis of lung carcinoma, carcinomas metastatic to lung and pleura, and pleural malignant mesothelioma. Am. J. Clin. Path. 95:322-329, 1991

Stahel, R A (Chairman). Third International IASLC Workshop on Lung Tumor and Differentiation Antigens. Inter. J. Cancer Suppl 8:6-26, 1994.

Wang Q, VanDusen W J, Petroski C J, Garsky V M, Stern A M, and P A Freidman. Bovine liver aspartyl beta-hydroxylase. J. Biol. Chem. 266:14004-14010, 1991.

Xu, N., Chen, C-Y A, Shyu, A-B. Modulation of the fate of cytoplasmic mRNA by AU-rich elements: Key sequence features controlling mRNA deadenylation and decay. Mol. Cell. Biology. 17:4611-4621, 1997.

The invention claimed is:

1. An isolated cDNA molecule with a nucleotide sequence selected from the group of nucleotide sequences consisting of SEQ ID NO: 1, and a segment of the isolated cDNA molecule having SEQ ID NO: 1 wherein the segment extends from the start codon (ATG) to the stop codon TAA in the nucleotide sequence and includes 765 base pairs.

2. A vector comprising an isolated cDNA molecule of claim 1.

3. A vector comprising an isolated cDNA molecule encoding SEQ ID NO: 2.

4. A cDNA molecule that encodes a peptide consisting of the amino acid sequence selected from the group consisting of APPEDNPVED (SEQ ID NO: 6), EEQQEVPPDT (SEQ ID NO: 7), DGPTGEPQQE (SEQ ID NO: 8), EQENPDSSEPV (SEQ ID NO: 9) and PTGEPQ (SEQ ID NO: 10).

* * * * *